United States Patent [19]
van Boeckel et al.

[11] Patent Number: 4,719,202
[45] Date of Patent: Jan. 12, 1988

[54] DISACCHARIDE AND TRISACCHARIDE DERIVATIVES OF THE "LIPID A" TYPE

[75] Inventors: Constant A. A. van Boeckel, Oss; Tom Beetz, Lith, both of Netherlands

[73] Assignee: Akzo N.V., Arnhem, Netherlands

[21] Appl. No.: 828,277

[22] Filed: Feb. 11, 1986

[30] Foreign Application Priority Data

Feb. 22, 1985 [NL] Netherlands ............... 8500499

[51] Int. Cl.$^4$ ............... A61K 31/70; C07H 5/04
[52] U.S. Cl. ............... 514/61; 514/53; 514/62; 536/17.2; 536/17.9; 536/18.7
[58] Field of Search ............... 536/17.2, 17.9, 18.7; 514/53, 61, 62

[56] References Cited
U.S. PATENT DOCUMENTS 4,515,782  5/1985  Schaub et al. ............... 536/4.1

FOREIGN PATENT DOCUMENTS

81/02576  9/1981  PCT Int'l Appl. .

OTHER PUBLICATIONS

Chem. Abstracts 100, No. 21, p. 667, 175 177y (1984) (Makoto, et al, Agric. Biol. Chem. 48(1), 251-2 (1984)).
Chem. Abstracts 97, No. 23, (1982) p. 342, 195738e (Hori et al., Tanpakushitsu Kakusan Koso, 27(13) 1962-83 (1982)).

Primary Examiner—J. R. Brown
Assistant Examiner—Elli Peselev
Attorney, Agent, or Firm—William M. Blackstone

[57] ABSTRACT

The present invention is dealing with certain disaccharide or trisaccharide derivatives of the lipid A type, which have interesting immuno-modulating, more particularly immuno-stimulating properties.

19 Claims, No Drawings

DISACCHARIDE AND TRISACCHARIDE DERIVATIVES OF THE "LIPID A" TYPE

The invention relates to novel disaccharide and trisaccharide derivatives of the "Lipid A" type, to processes for the preparation thereof, to the use thereof as immuno-modulators and furthermore to pharmaceutical preparations which contain these derivatives as the active constituent.

By "Lipid A" there is meant the glycophospholipid moiety of lipopolysaccharides. Lipopolysaccharides are biopolymers which occur in the cell walls of Gram-negative bacteria. It is known from the literature that the basic skeleton of "Lipid A" is a β-1,6-coupled D-glucosamine-disaccharide, of which the amino groups and a number of the hydroxyl groups are esterified with fatty acids. Among the fatty acid radicals occurring in "Lipid A" there are, inter alia, those derived from saturated fatty acids, such as, for example, tetradecanoic acid, and also in particular those derived from β-hydroxy-fatty acids, such as, for example, 3-hydroxy-tetradecanoic acid and 3-hydroxy-hexadecanoic acid, of which the β-hydroxyl group is also often acylated with a fatty acid. "Lipid A" is not a single substance but a mixture, the composition of which moreover depends on the species. The precise structure of "natural Lipid A" derivatives has hitherto not been elucidated.

However, it is known that "natural Lipid A" fractions possess immunobiological effects. A shortcoming is that these "natural" mixtures are often toxic.

To illustrate the state of the art, the following literature may be cited: J. Biol. Chem. 257 (19), p. 11808–11815 (1982); Recl. Trav. Chim. Pays-Bas 102, p. 438–449 (1983); Tetrahedron Letters 24 (19), p. 2011–2014 (1983); Proceedings 7th Int. Symp. on Glycoconjugates, Lund-Ronneby, July 17–23, 1983, Ed. M. A. Chester et al., p. 281; Eur. J. Biochem. 137, p. 325–332 (1983); Infection and Immunity, Aug. 1983, p. 758–773.

A novel group of disaccharide and trisaccharide derivatives of the "Lipid A" type, having interesting immuno-modulating properties, has now been found.

The present invention therefore relates to novel disaccharide and trisaccharide derivatives of the "Lipid A" type, having the general formula I

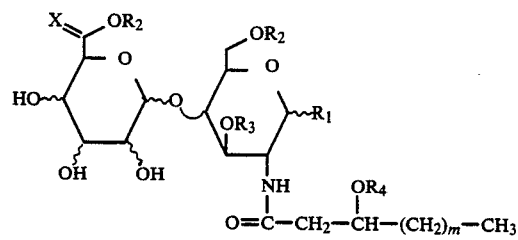

wherein $R_1$=OH, the group O—(CH$_2$)$_n$—CH$_3$ or a β-1,6-bonded glucosamine derivative having the formula II

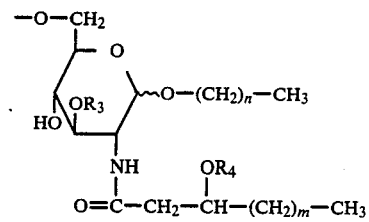

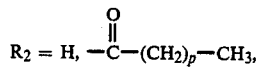

$R_2$ = H, —C(=O)—(CH$_2$)$_p$—CH$_3$,

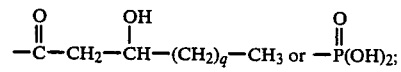

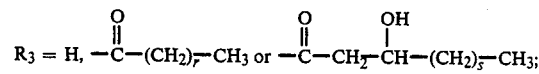

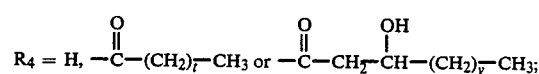

m, q, s, and v each independently is 6–14 n, p, r and t each independently is 0–16, and

X represents two hydrogen atoms or—when $R_2$=H—also oxygen, as well as pharmaceutically acceptable salts thereof.

Preferred compounds of formula I are compounds of the formula III

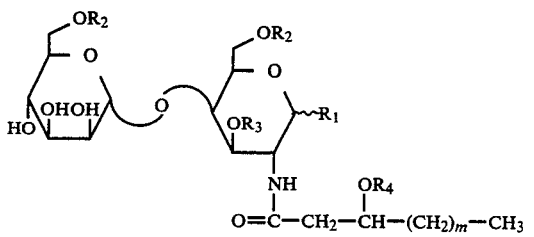

in which $R_1$, $R_2$, $R_3$, $R_4$ and m have the meanings above indicated, as well as pharmaceutically acceptable salts thereof.

The novel glycolipids of the formula I are capable of influencing the immune system in man and animals and in particular have an immuno-stimulant action. They are, for example, able to stimulate the immune-response to antigens (adjuvant activity). They can advantageously be used as anti-tumor agents, for example as agents for activating macrophages or for increasing the non-specific resistance of the body. They are capable of stimulating the reticulo-endothelial system and of increasing the phagocytotic and glycolytic activity of granulocytes and monocytes. They can favourably influence the bactericidal properties of blood and are moreover capable of stimulating the body to produce endogeneous mediators such as interferon, interleukines and tumour-necrosis factor. In addition these glycolipids show synergistic immuno-potentiating activity with cell wall components e.g. muramyl dipeptide (MDP), mycobacterial cell wall skeleton (CWS) and other biological response modifiers (e.g. interferons, interleukines, TNF).

The novel glycolipids can be prepared in a manner which is obvious per se, starting from suitable simple sugars (monosaccharides), which are α- or β-coupled in the correct manner, or from a suitable (1→4)-coupled disaccharide which is optionally further β-(1→6)-coupled with a monosaccharide, after which, in both cases, the desired substituents are still introduced into the end product. Monosaccharides and disaccharides which can be used as starting materials are for example D-mannose, D-glucose, other D-aldopyranoses and 4-0-(D-manno-pyranosyl)-D-glucose derivatives having reactive groups, suitable for α- or β-coupling, for example a bromine atom in position 1 and a free hydroxyl group in position 4 or 6. Other hydroxyl groups present in the molecule are protected in a suitable manner by esterification or etherification.

Suitable protective groups are, for example, acyl groups, such as acetyl, levulinoyl and chloroacetyl, and hydrocarbyl groups, such as methyl, propyl, butyl, allyl and benzyl. In choosing these groups, it is possible to proceed selectively, that is to say the choice of the protective group in a particular position takes into account the substituent which has to be present in this position in the end product.

For example, acetyl and allyl are used so that they can be removed selectively after the coupling reaction, in order to be able to introduce, into these positions, the substituents desired in the end products. Benzyl is preferably used to protect hydroxyl groups which do not need to participate in the coupling reaction or reactions and the subsequent selective substitution reactions.

As the last step, the benzyl groups are removed by hydrogenolysis, for example in the presence of $H_2/Pd$.

Amino groups present in position 2 in the end products are preferably already present in the starting materials, but in that case they are in a protected form, for example as an azido group, phthalimido group or acylamino group. In the last-mentioned group, it is possible, where desired, to choose as the acyl group itself the fatty acid or β-hydroxy-fatty acid group desired in the end product.

Examples of monosaccharides and disaccharides which can be used as starting materials are methyl 2-azido-3,4-di-0-benzyl-2-deoxy-β-D-glucopyranoside, 3-0-allyl-1,6-anhydro-2-azido-2-deoxy-β-D-glucopyranose, 6-0-acetyl-2,3,4-tri-0-benzyl-α-D-mannopyranosyl bromide, 6-0-acetyl-4-0-(6-0-acetyl-2,3,4-tri-0-benzyl-β-D-mannopyranosyl)-2-azido-3-0-benzyl-2-deoxy-β-D-glucopyranosyl bromide, 6-0-acetyl-4-0-(6-0-acetyl-2,3,4-tri-0-benzyl-β-D-mannopyranosyl)-3-0-allyl-2-azido-2-deoxy-α-D-gluco-pyranosyl bromide and benzyl 6-0-acetyl-4-0-(6-0-acetyl-2,3,4-tri-0-benzyl-β-D-mannopyranosyl)-3-0-allyl-2-azido-2-deoxy-β-D-glucopyranoside.

Starting materials which are not commercially available or are not described in the literature can be prepared from well-known monosaccharides or disaccharides in a manner known per se. This is illustrated in the examples.

The coupling reaction is carried out in the presence of a silver salt, for example silver carbonate, silver triflate or silver silicate, if desired in the presence of a molecular sieve. The use of "silver zeolite" (Acta. Chem. Scand. B 37 (1983), 249) is very advantageous for β-coupling.

The ring opening of 1,6-anhydro intermediates is usually carried out with a mixture of acetic anhydride and trifluoroacetic acid. Instead of this, it is however also possible to use other acid mixtures, for example acetic anhydride+$BF_3$ or acetic anhydride+sulphuric acid.

The removal of an anomeric acetyl group can for example be carried out with hydrazine/acetic acid in a suitable solvent, for example dimethylformamide. This hydrolysis can also be carried out with other amines, for example benzylamine or piperidine, in tetrahydrofuran.

The conversion of the anomeric hydroxyl group to the bromide can be carried out with any Vilsmeyer salt having the formula:

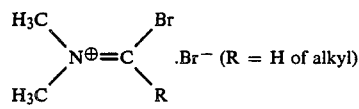

in a suitable solvent, for example chloroform, methylene chloride or ethylene chloride. The Vilsmeyer salt can be formed in situ, for example from oxalyl bromide and dimethylformamide or dimethylacetamide.

If desired, an anomeric acetyl group can also be directly reacted to the bromide, for example with the aid of $TiBr_4$/ethyl acetate in methylene chloride.

Hydrolysis of acyl groups, for example an acetyl group in position 6, can be carried out with any base, for example with KOH, potassium t.-butylate or triethylamine in methanol.

The selective reduction of azido groups to amino groups can advantageously be carried out with $H_2S$ in pyridine. This reduction can also be carried out with $NiCl_2/NaBH_4$ or, optionally, in two steps by first treating the product to be reduced with triethyl phosphite and thereafter with an acid.

The acylation of an amino group can be carried out with the appropriate carboxylic acid in accordance with standard methods, for example in the presence of dicyclohexylcarbodiimide in an inert solvent, for instance dioxane or tetrahydrofuran. In place of the carboxylic acid, it is also possible to use a derivative of the carboxylic acid, for example the ester of the particular acid with N-hydroxybenzotriazole or with N-hydroxysuccinimide.

The acylation of a hydroxyl group with the appropriate carboxylic acid, for example of a hydroxyl group in position 1, 3 or 6 of a saccharide or in position 3 of an acyl group, can also be carried out in accordance with standard methods, for example with the acid or the acid anhydride in the presence of dicyclohexylcarbodiimide and/or N,N-dimethylaminopyridine, or with the acid chloride in pyridine.

Removal of a protective allyl group can be carried out with palladium chloride in acetic acid; if desired it can also be carried out by first isomerising the allyl group with the aid of an iridium or rhodium catalyst, and then splitting off the propenyl group with $HgCl_2/HgO$ or with an acid.

As regards the substituents $R_1$ to $R_4$ inclusive, the following should also be noted:

If the end product is a disaccharide, then $R_1$ is preferably OH. If the end product is a trisaccharide, $R_1$ is of course a β-1,6-bonded glucosamine derivative of the formula I, wherein n is preferably 1. In the acylamino group, m is preferably 10.

$R_2$ is preferably H or

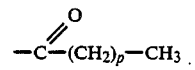

$R_3$ is preferably H or

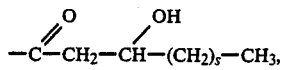

wherein s is preferably 10.

If $R_4$ is

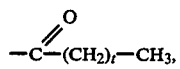

then t is preferably 6 and if $R_4$ is

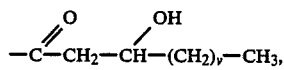

then v is preferably 10.

Examples of acyl groups which can be present in position 6($R_2$) are acetyl (p=0), propionyl (p=1), butyryl (p=2), octanoyl (p=6), tetradecanoyl (p=12) and (R)-3-hydroxy-tetradecanoyl (q=10).

Examples of acyl groups which can present in position 3($R_3$) are dodecanoyl (r=10), tetradecanoyl (r=12) and (R)-3-hydroxy-tetradecanoyl (s=10).

Examples of N-acyl groups are (R)-3-hydroxy-dodecanoyl (m=8), (R)-3-hydroxy-tetradecanoyl (m=10), (R)-3-hydroxy-hexadecanoyl (m=12) and 3-acyloxy derivatives thereof. Examples of such 3-acyloxy derivatives (—OR$_4$) are octanoyloxy (t=6), tetradecanoyloxy (t=12), (R)-3-hydroxy-dodecanoyloxy (v=8), (R)-3-hydroxy-tetradecanoyloxy (v=10) and (R)-3-hydroxy-hexadecanoyloxy (v=12).

The pharmaceutical salts of the compounds of formula I are alkali or earth alkali-metal salts such as sodium, potassium, lithium or calcium salts. These salts are possible if X is oxygen and/or if OR$_2$ represents a phosphate moiety.

The novel compounds according to the invention can be employed both enterally (for example orally or rectally) and parenterally. For this purpose, they are usually mixed with pharmaceutical auxiliaries and then administered in the form of tablets, pills, dragees, pastilles, powders, (micro)-capsules, sprays, suppositories, ointments, emulsions, suspensions or solutions. The pharmaceutical preparations are produced in accordance with known galenical methods. Parenteral administration is usually carried out with the aid of a syringe, by means of which an emulsion, suspension or solution, containing the active substance, is administered subcutaneously, intramuscularly or intravenously.

The usual daily dose, which can vary depending on the active substance used and on the condition to be treated, is preferably between 0.001–1 mg/kg bodyweight for oral or rectal administration and between 0.1 μg–0.5 mg/kg bodyweight for parenteral administration.

The examples which follow illustrate the invention.

EXAMPLE I (a) 0.4 ml of methanol, 0.614 g of Ag$_2$CO$_3$ and 0.9 g of a 3 Å molecular sieve were added to a solution of 0.98 g of 6-0-acetyl-2-azido-3,4-di-0-benzyl-2-deoxy-α-D-glucopyranosyl bromide in 6.5 ml of CH$_2$Cl$_2$. After the mixture had been stirred for 16 hours at room temperature, 50 ml of CH$_2$Cl$_2$ were added. The mixture was filtered over Hyflo. The organic layer was evaporated and the residue was purified by chromatography over silica gel. Yield, 0.75 g of methyl 6-0-acetyl-2-azido-3,4-di-0-benzyl-2-deoxy-β-D-glucopyranoside. $^1$H-NMR (CDCl$_3$): δ=4.17 (d, J$_{1,2}$=7.8 Hz, 1H); δ=3.56 (s, OCH$_3$).

(b) 0.65 g of methyl 6-0-acetyl-2-azido-3,4-di-0-benzyl-2-deoxy-β-D-glucopyranoside was dissolved in a mixture of 5 ml of methanol and 1 ml of dioxane. 15 mg of potassium t.-butylate were added to this mixture, after which it was stirred for 1 hour at room temperature. After addition of 0.5 ml of acetic acid, the mixture was taken up in 100 ml of CH$_2$Cl$_2$. After washing with 50 ml of water, the organic layer was evaporated. Yield, 0.58 g of methyl 2-azido-3,4-di-0-benzyl-2-deoxy-β-D-glucopyranoside, melting point 122° C., [α]$_D^{20}$=−39 (c=1, CH$_2$Cl$_2$).

EXAMPLE II (a) 0.42 ml of hydrazine hydrate and 0.48 ml of acetic acid were added to a solution of 3.0 g of 1,6-di-0-acetyl-4-0-(6-0-acetyl-2,3,4-tri-0-benzyl-β-D-manno-pyranosyl)-2-azido-3-0-benzyl-2-deoxy-α-D-glucopyranose in 60 ml of dimethylformamide. The reaction mixture was stirred for 1 hour at room temperature. Dimethylformamide was evaporated off under a high vacuum. The residue was taken up in 200 ml of CH$_2$Cl$_2$. After washing with a saturated NaHCO$_3$ solution (50 ml) and water (50 ml), the organic layer was evaporated. The residue obtained was chromatographed over a silica gel column. Yield, 2.42 g of 6-0-acetyl-4-0-(6-0-acetyl-2,3,4-tri-0-benzyl-β-D-mannopyranosyl)-2-azido-3-0-benzyl-2-deoxy-α-D-glucopyranose, $^1$H-NMR (CDCl$_3$): δ=5.25 (d, J$_{1,2}$=3.5 Hz, 1H).

(b) A solution of 0.864 g of oxalyl bromide in 4 ml of chloroform was slowly added dropwise, in a nitrogen atmosphere, to a solution of 1.73 g of the disaccharide of Example IIa in a mixture of 20 ml of dry chloroform and 4 ml of dimethylformamide. The whole was stirred for 1 hour at room temperature, after which 150 ml of diethyl ether were added. The precipitate obtained was filtered off and the filtrate was washed with 50 ml of cold sodium bicarbonate solution (1%) and then with 50 ml of cold water. The organic layer was dried over MgSO$_4$, filtered and evaporated in vacuo. Yield, 1.84 g of 6-0-acetyl-4-0-(6-0-acetyl-2,3,4-tri-0-benzyl-β-D-mannopyranosyl)-2-azido-3-0-benzyl-2-deoxy-α-D-glucopyranosyl bromide, $^1$H-NMR (CDCl$_3$): δ=6.34 (d, J$_{1,2}$=4,5 Hz, 1H); δ=4.41 (d, J$_{1,2}$=0.5 Hz, 1H').

EXAMPLE III (a) A solution of 1.84 g of 6-0-acetyl-4-0-(6-0-acetyl-2,3,4-tri-0-benzyl-β-D-mannopyranosyl)-2-azido-3-0-benzyl-2-deoxy-α-D-glucopyranosyl bromide in 3 ml of methylene dichloride was added dropwise to a solution of 0.677 g of methyl 2-azido-3,4-di-0-benzyl-2-deoxy-β-D-glucopyranoside in 3 ml of methylene dichloride in the presence of 4 g of "silver zeolite" (Acta. Chem. Scand. (1983), 249). Thereafter, the mixture was stirred for 60 hours at room temperature in a nitrogen atmosphere. After addition of 50 ml of methylene dichloride, the mixture was filtered over Hyflo. The solvent was removed by evaporation and the residue was purified by chromatography over a silica gel column. Yield, 1.35 g of methyl 0-6-0-acetyl-2,3,4-tri-0-benzyl-β-D-mannopyranosyl-(1→4)-0-6-0-acetyl-2-azido-3-0-benzyl-2-deoxy-β-D-glucopyranosyl-(1→6)-0-2-azido-3,4-di-0-benzyl-2-deoxy-β-D-glucopyranoside, an oil; $^1$H-NMR (CDCl$_3$): δ=4.19 (d, J$_{1,2}$=3.5 Hz, 1H); δ=4.32 (d, J$_{1,2}$=3.5 Hz, 1H'); δ=4.43 (s, 1H'').

(b) 0.02 g of potassium t.-butylate was added to a solution of 0.966 g of the methylglucopyranoside of Example III(a) in a mixture of 2.35 ml of methanol and 3.3 ml of dioxane. The mixture was stirred for 20 minutes at room temperature, after which 0.2 ml of acetic acid was added, followed by 100 ml of methylene dichloride. The mixture obtained was washed twice with 50 ml of water and the organic layer was then evaporated. Yield, 0.898 g of methyl 0-2,3,4-tri-0-benzyl-β-D-mannopyranosyl-(1→4)-0-2-azido-3-0-benzyl-2-deoxy-β-D-glucopyranosyl-(1→6)-0-2-azido-3,4-di-0-benzyl-2-deoxy-β-D-glucopyranoside in the form of an oil.

(c) H$_2$S was passed for 3 hours, at room temperature, through a solution of 0.649 g of the methylglucopyranoside of Example III(b) in a mixture of 13.5 ml of pyridine and 3.75 ml of water. The mixture was then stirred for 16 hours. 2 ml of acetic acid were added to the reaction mixture, followed by 100 ml of CH$_2$Cl$_2$. The mixture obtained was washed twice with 50 ml of an 0.1N sodium hydroxide solution. The organic layer was evaporated. The residue was purified by chromatography over a silica gel column (CH$_2$Cl$_2$/methanol 9/1). Yield, 0.572 g of methyl 0-2,3,4-tri-0-benzyl-β-D-mannopyranosyl-(1→4)-0-2-amino-3-0-benzyl-2-deoxy-β-D-glucopyranosyl-(1→6)-0-2-amino-3,4-di-0-benzyl-2-deoxy-β-D-glucopyranoside, in the form of an oil.

(d) 0.572 g of the methylglucopyranoside of Example III(c) and 0.382 g of (R)-3-hydroxy-tetradecanoic acid were dissolved in 8 ml of dioxane. The pH of this solution was brought to 7 with N-ethylmorpholine, after which 0.322 g of dicyclohexylacarbodiimide was added. The mixture was stirred for 2 hours. Thin-layer chromatography of a specimen showed that in addition to N-acylation some O-acylation had also occurred.

The reaction mixture was filtered and 100 ml of CH$_2$Cl$_2$ were added to the filtrate. The mixture obtained was successively washed with an aqueous 1% strength NaHCO$_3$ solution, water and an aqueous 1% strength AgNO$_3$ solution. The organic layer was evaporated and the residue was dissolved in a mixture of 5 ml of dioxane and 10 ml of methanol. In order to hydrolyse the O-acylated products, 0.02 g of potassium t.-butylate was added to this mixture, after which it was stirred for 1 hour. 100 ml of CH$_2$Cl$_2$ were added to the e mixture obtained and the whole was washed twice with 50 ml of water. The organic layer was evaporated and the residue was purified by chromatography over silica gel (CH$_2$Cl$_2$/methanol 9/1). Yield, 0.717 g of methyl 0-2,3,4-tri-0-benzyl-β-D-mannopyranosyl-(1→4)-0-3-0-benzyl-2-deoxy-2-[(R)-3-hydroxy-1-oxo-tetradecyl)amino]-β-D-glucopyranosyl-(1→6)-0-3,4-di-0-benzyl-2-deoxy-2-[(R)-3-hydroxy-1-oxo-tetradecyl)amino]-β-D-glucopyranoside, melting point 134°–135° C., [α]$_D^{20}$=−25.6 (CHCl$_3$).

(e) 0.224 g of the N-acylated product obtained in Example III(d) was dissolved in a mixture of 16 ml of ethanol, 16 ml of ethyl acetate and 1 ml of acetic acid. 200 mg of 10% Pd on charcoal were added to this mixture, and the mixture was stirred for 16 hours while H$_2$ at atmospheric pressure was passed through it. The catalyst was filtered off and the filter cake was rinsed with dimethylformamide. The filtrate was evaporated and the residue was purified by gel permeation chromatography on an LH-20 column, with dimethylformamide. Yield, 0.128 g of methyl 0-β-D-mannopyranosyl-(1→4)-0-2-deoxy-2-[((R)-3-hydroxy-1-oxo-tetradecyl)amino]-β-D-glucopyranosyl-(1→6)-0-2-deoxy-2-[((R)-3-hydroxy-1-oxo-tetradecyl)-amino]-β-D-glucopyranoside, melting point 218°–221° C. (decomposition), [α]$_D^{20}$=−25.1 (dimethylformamide).

EXAMPLE IV (a) 0.25 g of the N-acylated product obtained in Example III(d) was dissolved in a mixture of 3.5 ml of CH$_2$Cl$_2$ and 0.5 ml of pyridine. 0.3 ml of octanoic acid anhydride and 20 mg of 4-N,N-dimethylaminopyridine were added to this mixture at 50° C., under nitrogen. The temperature was slowly brought to room temperature after which the mixture was stirred for a further 16 hours. 100 ml of CH$_2$Cl$_2$ were added to the reaction mixture, after which the whole was successively washed with 50 ml of a 5% strength NaHCO$_3$ solution and with 50 ml of water. The organic layer was evaporated and the residue was purified by chromatography over silica gel (CH$_2$Cl$_2$/acetone 92/9). Yield, 0.308 g of methyl 0-2,3,4-tri-0-benzyl-6-0-(1-oxo-octyl)-β-D-mannopyranosyl-(1→4)-0-3-0-benzyl-2-deoxy-6-0-(1-oxo-octyl)-2-[((R)-3-(1-OxO-octyloxy)-1-oxotetradecyl)amino]-β-D-glucopyranosyl-(1→6)-3,4,-di-0-benzyl-2-deoxy-2-[(RR)-3-(1-OxO-octyloxy)-1-oxotetradecyl)amino]-β-D-glucopyranoside, an oil with [α]$_D^{20}$=−6.2 (CHCl$_3$).

(b) 0.22 g of the product obtained in Example IV(a) was dissolved in a mixture of 14.5 ml of isopropanol, 2.5 ml of dimethylformamide and 0.5 ml of acetic acid. 280 mg of 10% Pd on charcoal were added to this mixture, which was then hydrogenolysed for 16 hours at atmospheric pressure. The catalyst was filtered off and rinsed with 50 ml of pyridine/methanol (1/1, v/v). The filtrate was evaporated and the residue was freeze-dried from 10 ml of isobutanol/water (9/1, v/v). Yield, 0.124 g of methyl 0-6-0-(1-oxo-octyl)-β-D-mannopyranosyl-(1→4)-0-2-deoxy-6-0-(1-oxo-octyl)-2-[((R)-3-(1-oxo-octyloxy)-1-1oxo-tetradecyl)-amino]-β-D-glucopyranosyl-(1→6)-0-2-deoxy-2-[((R)-3-(1-OxO-octyloxy)-1-oxotetradecyl)amino]-β-D-glucopyranoside, melting point 190°–192° C. (decomposition), [α]$_D^{20}$=−12.8 (methanol/CH$_2$Cl$_2$, 1/1, v/v).

EXAMPLE V (a) 0.34 g (1.5 mmol) of 3-0-allyl-1,6-anhydro-2-azido-2-deoxy-β-D-glucopyranose together with 500 mg of silver silicate and 300 mg of ground molecular sieve (4 Å) were stirred for 2 hours in 1 ml of methylene dichloride. 0.87 g of 6-0-acetyl-2,3,4-tri-0-benzyl-α-D-mannopyranosyl bromide in 10 ml of methylene chloride were added dropwise to this mixture at room temperature, and the reaction mixture was stirred for 3 hours. After addition of 60 ml of methylene chloride, the mixture was filtered over Hyflo, washed with water and evaporated. The residue was chromatographed . Yield, 0.75 g of 4-0-(6-0-acetyl-2,3,4-tri-0-benzyl-β-D-mannopyranosyl)-3-0-allyl-1,6-anhydro-2-azido-2-deoxy-β-D-glucopyranose.

(b) 1.8 ml of trifluoroacetic acid were added with stirring, at 0° C., to a solution of 0.75 g of the product obtained in Example V(a) in 18 ml of acetic anhydride. The reaction mixture was allowed to come slowly to room temperature. After 2 hours, the mixture was subjected to thin-layer chromatography (toluene/acetone 4:1, v:v). The syrup obtained was dissolved in methylene chloride and the solution was washed with water, dried over MgSO$_4$ and evaporated. The residue was purified by chromatography over silica gel. Yield, 0.62 g of 1,6-diacetyl-4-0-(6-0-acetyl-2,3,4-tri-0-benzyl-β-D-mannopyranosyl)-3-0-allyl-2-azido-2-deoxy-α-D-glucopyranose.

(c) The product of Example V(b) was converted to 6-0-acetyl-4-0-(6-0-acetyl-2,3,4-tri-0-benzyl-β-D-mannopyranosyl)-3-0-allyl-2-azido-2-deoxy-α-D-glucopyranosyl bromide in a similar manner to that described in Example II.

(d) 0.42 g of the bromide obtained in Example V(c) was dissolved in 1 ml of toluene. The following were added successively to this solution at 0° C.: 0.5 g of silver silicate, 0.25 g of ground molecular sieve (4 Å) and 2.5 mmol of benzyl alcohol. The mixture was stirred for 4 hours at 0° C. 50 ml of $CH_2Cl_2$ were added to the reaction mixture, which was then filtered over Hyflo. The filtrate was evaporated and the residue was purified over a silica gel column. Yield, 0.35 g of benzyl 6-0-acetyl-4-0-(6-0-acetyl-2,3,4-tri-0-benzyl-β-D-mannopyranosyl)-3-0-allyl-2-azido-2-deoxy-β-D-glucopyranoside, $^1$H-NMR ($CDCl_3$) $\delta=4.30$ (d, $J_{1,2}=7.8$ Hz, 1H).

(e) The azido compound obtained in Example V(d) was reduced to the corresponding amino compound in a similar manner to that described in Example III(c) and (d) and the product thus obtained was N-acylated with (R)-3-hydroxy-tetradecanoic acid. Yield, 0.33 g of benzyl 6-0-acetyl-4-0-(6-0-acetyl-2,3,4-tri-0-benzyl-β-D-mannopyranosyl)-3-0-allyl-2-deoxy-2-[((R)-3-hydroxy-1-oxo-tetradecyl)amino]-β-D-glucopyranoside.

(f) 60 mg of sodium acetate and 65 mg of palladium chloride were added, under nitrogen, to a solution of 0.33 g of the product of Example V(e) in 0.6 ml of acetic acid and 0.03 ml of water. After it had been stirred for 35 hours at room temperature, the reaction mixture was taken up in 50 ml of methylene chloride. The solution was washed with a 5% $NaHCO_3$ solution, after which the organic layer was evaporated and the residue was purified on a silica gel column. Yield, 0.25 g of benzyl 6-0-acetyl-4-0-(6-0-acetyl-2,3,4-tri-0-benzyl-β-D-mannopyranosyl)-2-deoxy-2-[((R)-3-hydroxy-1-oxo-tetradecyl)amino]-β-D-gluco-pyranoside.

(g) 1 mmol of (R)-3-benzyloxytetradecanoic acid, 1 mmol of dicyclohexylcarbodiimide and a catalytic amount of N,N-dimethylaminopyridine were added to a solution of 0.25 g of the product of Example V(f) in 2 ml of methylene dichloride. The mixture was stirred for 16 hours. After filtration, 50 ml of methylene dichloride were added and the mixture was worked up as described in Example V(b). Yield, 0.29 g of benzyl 6-0-acetyl4-0-(6-0-acetyl-2,3,4-tri-0-benzyl-β-D-mannopyranosyl)-3-0-[((R)-3-benzyloxy-1-oxo-tetradecyl]-2-[((R)-3-((R)-3-benzyloxy-1-oxo-tetradecyloxy)-1-oxo-tetradecyl)amino]-2-deoxy-β-D-glucopyranoside.

(h) The product of Example V(g) was hydrogenated with $H_2$/Pd, in a similar manner to that described in Example III(e), in order to remove the benzyl groups, Yield, 0.12 g of 6-0-acetyl-4-0-(6-0-acetyl-β-D-mannopyranosyl)-2-deoxy-3-0-[(R)-3-hydroxy-1-oxo-tetradecyl]-2-[((R)-3-((R)-3-hydroxy-1-oxo-tetradecyloxy)-1-oxo-tetradecyl)amino]-β-D-glucopyranose, $\delta=5.14$ (d, $J_{1,2}=3.3$ Hz, 1H), $\delta=4.72$ (s, 1H).

EXAMPLE VI

The product of Example V(f) was hydrogenated with $H_2$/Pd, in a similar manner to that described in Example III(e), to removed the benzyl groups. Yield, 0.18 g of 6-0-acetyl-4-0-(6-0-acetyl-β-D-mannopyranosyl)-2-deoxy-2-[((R)-3-hydroxy-1-oxo-tetradecyl)amino]-β-D-glucopyranose.

EXAMPLE VII (a) The bromide of Example II(b) was converted to benzyl 6-0-acetyle product of Example V(g) was hydrogenated with $H_2$/Pd, in a similar manner to that described in Example III(e), order to remove the benzyl groups, Yield, 0.12 g of 6-0-acetyl-4-0-(6-0-acetyl-β-D-mannopyranosyl)-2-deoxy-3-0-[(R)-3-hydroxy-1-oxo-tetradecyl]-2-[((R)-3-((R)-3-hydroxy-1-oxo-tetradecyloxy)-1-oxo-tetradecyl)amino]-β-D-glucopyranose, $\delta=5.14$ (d, $J_{1,2}=3.3$ Hz, 1H), $\delta=4.72$ (s, 1H).

EXAMPLE VI

The product of Example V(f) was hydrogenated with $H_2$/Pd, in a similar manner to that described in Example III(e), to remove the benzyl groups. Yield, 0.18 g of 6-0-acetyl-4-0-(6-0-acetyl-β-D-mannopyranosyl)-2-deoxy-2-[((R)-3-hydroxy-1-oxo-tetradecyl)amino]-β-D-glucopyranose.

EXAMPLE VII (a) The bromide of Example II(b) was converted to benzyl 6-0-acetyl-4-0-(6-0-acetyl-2,3,4-tri-0-benzyl-β-D-mannopyranosyl)-2-azido-3-0-benzyl-2-deoxy-β-D-glucopyranoside in a similar manner to that described in Example V(d).

(b) The product of Example VII(a) was converted to benzyl 2-azido-3-0-benzyl-4-0-(2,3,4-tri-0-benzyl-β-D-mannopyranosyl)-2-deoxy-β-D-glucopyranoside in a similar manner to that described in Example III(b).

(c) The product of Example VII(b) was reduced to benzyl 2-amino-3-0-benzyl-4-0-(2,3,4-tri-0-benzyl-β-D-mannopyranosyl-2-deoxy-β-D-glucopyranoside in a similar manner to that described in Example III(c).

(d) The product of Example VII(c) was N-acylated with (R)-3-((R)-3-hydroxy-1-oxo-tetradecyloxy)-tetradecanoic acid, in a similar manner to that described in Example III(d), to give benzyl 4-0-(2,3,4-tri-0-benzyl-β-D-mannopyranosyl)-2-deoxy-2-[((R)-3-((R)-3-hydroxy-1-oxo-tetradecyloxy)-1-oxo-tetradecyl)amino]-β-D-glucopyranoside.

(e) The product of Example VII(d) was hydrogenated with $H_2$/Pd, in a similar manner to that described in Example III(e), to remove the benzyl groups. The end product was 2-deoxy-2-[((R)-3-((R)-3-hydroxy-1-oxo-tetradecyloxy)-1-oxo-tetradecyl)amino]-4-0-β-D-mannopyranosyl-β-D-glucopyranose.

EXAMPLE VIII (a) The product of Example V(c) was β-1,6-coupled with methyl 3-0-allyl-2-azido-4-0-benzyl-2-deoxy-β-D-glucopyranoside in a similar manner to that described in Example III(a), after which the coupling product was converted to methyl 0-6-0-acetyl-2,3,4-tri-0-benzyl-β-D-mannopyranosyl-(1→4)-0-6-0-acetyl-3-0-allyl-2-deoxy-2-[((R)-3-hydroxy-1-oxotetradecyl)amino]-β-D-glucopyranosyl-(1→6)-0-3-0-allyl-4-0-benzyl-2-deoxy-2-[((R)-3-hydroxy-1-oxotetradecyl)amino]β-D-glucopyranoside in a similar manner to that described in Example III(c) and (d).

(b) The product of Example VIII(a) was converted to methyl 0-6-0-acetyl-β-D-mannopyranosyl-(1→4)-0-6-0-acetyl-2-deoxy-3-0-[(R)-3-hydroxy-1-oxotetradecyl]--2-[((R)-3-((R)-hydroxy-1-oxotetradecyloxy)-1-oxotetradecyl)-amino]-β-D-glucopyranosyl-(1→6)-0-2-deoxy-3-0-[(R)-3-hydroxy-1-oxotetradecyl]-2-[((R)-3-((R)-3-hydroxy-1-oxo-tetradecyloxy)-1-oxotetradecyl)amino]-β-D-glucopyranoside in a similar manner to that described in Example V(f)–(h), by removing the allyl groups, esterifying the free hydroxyl groups with (R)-3-benzyloxytetradecanoic acid and removing of the benzyl groups.

EXAMPLE IX (a) Methyl 0-2,3,4-tri-0-benzyl-β-D-mannopyranosyl-(1→4)-0-3-0-allyl-2-deoxy-2-[((R)-3-hydroxy-1-oxotetradecyl)amino]-β-D-glucopyranosyl-(1→6)-0-3-0-allyl-4-0-benzyl-2-deoxy-2-[((R)-3-hydroxy-1-oxotetradecyl)amino]-β-D-glucopyranoside was obtained in a similar manner to that described in Example VIII(a), but in which the intermediate hydrolysis step, as described in Example III(b), was carried out simultaneously.

(b) The product of Example IX(a) was converted to methyl 0-6-0-(1-oxo-octyl)-β-D-mannopyranosyl-(1→4)-0-2-deoxy-3,6-di-0-(1-oxo-octyl)-2-[((R)-3-(1-oxo-octyloxy)-1-oxotetradecyl)amino]-β-D-glucopyranosyl-(1→6)-0-2-deoxy-3-0-(1-oxo-octyl)2-[((R)-3-(1-oxo-octyloxy)-1-oxotetradecyl)amino]-β-D-glucopyranoside in a similar manner to that described in Example V(f)–(h), by removing the allyl groups, esterifying the free hydroxyl groups with octanoic acid and removing the benzyl groups.

EXAMPLE X (a) After de-acetylation of the compound obtained in Example Vd according to the method described in Example Ib, the crude product was dissolved in 10 ml DMF, after which 1.15 g bariumoxide, 0,34 g bariumhydroxide and 0.6 ml benzylbromide were added.

The reaction mixture was stirred for 24 hours at ambient temperature and then filtered over hyflo, after which 100 ml methylene chloride was added. The solution was washed with 1% acetic acid, whereupon on organic layer was evaporated and the residue obtained purified on a silica gel column.

Yield 0.34 g (oil) of benzyl 4-0-(2,3,4,6-tetra-0-benzyl-β-D-mannopyranosyl-3-0-allyl-6-0-benzyl-2-azido-2-deoxy-β-D-glucopyranoside, $[\alpha]_D^{20} = -26$ (c=1, CH$_2$Cl$_2$).

(b) The azido compound obtained above was reduced to the corresponding amino compound in a similar manner to that described in Example III(c) and (d) and the product thus obtained was N-acylated with (R)-3-benzyloxy-tetradecanoic acid. Yield, 0.31 g of benzyl 4-0-(2,3,4,6-tetra-0-benzyl-β-D-mannopyranosyl)-3-0-allyl-6-0-benzyl-2-deoxy-2-[((R)-3-benzyloxy-1-oxo-tetradecyl)amino]-β-D-glucopyranoside.

(c) 60 mg of sodium acetate and 65 mg of palladium chloride were added, under nitrogen, to a solution of 0.31 g of the product of (b) in 0.6 ml of acetic acid and 0.03 ml of water. After it had been stirred for 35 hours at room temperature, the reaction mixture was taken up in 50 ml of methylene chloride. The solution was washed with 5% NaHCO$_3$ solution, after which the organic layer was evaporated and the residue was purified on a silica gel column. Yield, 0.24 g of benzyl 4-0-(2,3,4,6-tetra-0-benzyl-β-D-mannopyranosyl)-6-0-benzyl-2-deoxy-2-[((R)-3-benzyloxy-1-oxo-tetradecyl)-amino]-β-D-glucopyranoside.

(d) 1 mmol of (R)-3-benzyloxytetradecanoic acid, 1 mmol of dicyclohexylcarbodiimide and a catalytic amount of N,N-dimethylaminopyridine were added to a solution of 0.24 g of the above product in 2 ml of methylene dichloride. The mixture was stirred for 16 hours. After filtration, 50 ml of methylene dichloride were added and the mixture was worked up as described in Example V. Yield, 0.27 g of benzyl 4-0-(2,3,4,6-tetra-0-benzyl-β-D-mannopyranosyl)-3-0-[((R)-3-benzyloxy-1-oxo-tetradecyl]-2-[((R)-3-benzyloxy-1-oxo-tetradecyl-amino]-2-deoxy-β-D-glucopyranoside.

(e) The above product was hydrogenated with H$_2$Pd, in a similar manner to that described in Example III(e), in order to remove the benzyl groups. Yield, 0.12 g of 4-0-(β-D-mannopyranosyl)-2-deoxy-3-0-[(R)-3-hydroxy-1-oxo-tetradecyl]-2-[((R)-3-hydroxy-1-oxotetradecyl)amino]-β-D-glucopyranose, δ=5.07 (d, $J_{1,2}$=3.6 Hz, 1H), δ=4.54 (s, 1H). Melting point=16-8°–174° C.; $[\alpha]_D^{20} = -25.6$ (methanol:CH$_2$Cl$_2$ 1:1).

EXAMPLE XI

The end product of Example 10(c) was O-acylated with tetradecanoic acid anhydride and hydrogenated with hydrogen and Pd/C resulting in the product: β-D-mannopyranosyl(1→4)-2-deoxy-2-[((R)-3-(1-oxo-tetradecyloxy)-1-oxotetradecyl)amino]-3-0-(1-oxotetradecyl)-β-D-glucopyranose, melting point 154°–157° C.; $[\alpha]_D^{20} = -19.3°$ (CHCl$_3$/methanol).

We claim:

1. A disaccharide or trisaccharide derivative of the Lipid A type, having the formula:

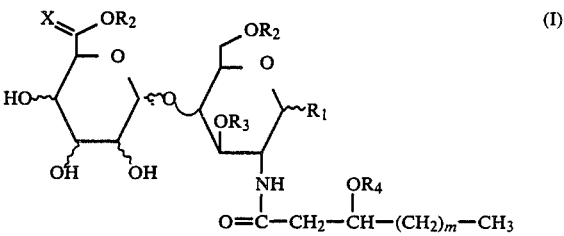

wherein

R$_1$=OH, the group —O(CH$_2$)$_n$—CH$_3$ or a β-1,6-bonded glucosamine derivative having the formula:

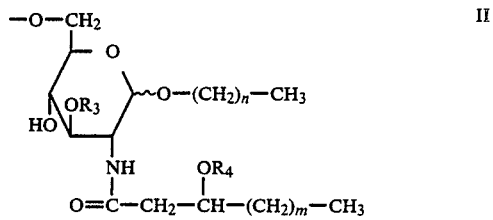

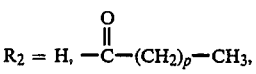

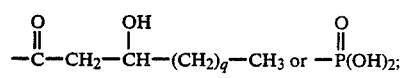

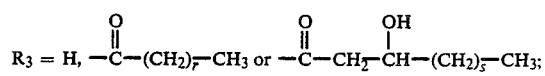

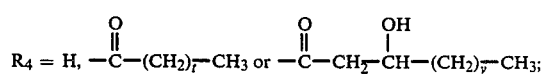

m, q, s and v each independently is 6–14 n, p, r and t each independently is 0–16, and

X represents two hydrogen atoms or—when $R_2=H$— also oxygen, as well as pharmaceutically acceptable salts thereof.

2. Compound according to claim 1, having the formula:

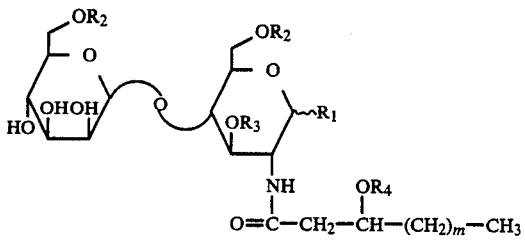

in which $R_1$, $R_2$, $R_3$, $R_4$ and m have the meanings indicated in claim 1.

3. Compound according to claim 1, wherein $R_1$ is OH.

4. Compound according to claim 1, wherein $R_1$ is a β-1,6-bonded glucosamine derivative having the formula (II) given in claim 1.

5. Compound according to claim 1, in which $m=10$.

6. Compound according to claim 1, wherein $X=2H$.

7. Compound according to claim 2, wherein $R_1$ is OH.

8. Compound according to claim 2, wherein $R_1$ is a β-1,6-bonded glucosamine derivative having the formula (II) given in claim 1.

9. Compound according to claim 2, in which $m=10$.

10. Compound according to claim 3 in which $m=10$.

11. Compound according to claim 4, in which $m=10$.

12. Compound according to claim 7, in which $m=10$.

13. Compound according to claim 8, in which $m=10$.

14. A pharmaceutical composition having an immuno-modulating action, which contains as active ingredient, an immuno-modulating effective amount of one or more compounds as defined in claim 1 in a pharmaceutically acceptable carrier.

15. A pharmaceutical composition having an immuno-modulating action which contains as active ingredient an immuno-modulating effective amount of one or more compounds as defined in claim 2 in a pharmaceutically acceptable carrier.

16. A pharmaceutical composition having an immuno-modulating effective amount of one or more compounds as defined in claim 3, in a pharmaceutically acceptable 17. A pharmaceutical composition having an immuno-modulating action which contains as active ingredient an immuno-modulating effective amount of one or more compounds as defined in claim 4 in a pharmaceutically acceptable carrier.

18. A pharmaceutical composition having an immuno-modulating action which contains as active ingredient, an immuno-modulating effective amount of one or more compounds as defined in claim 5 in a pharmaceutically acceptable carrier.

19. A pharmaceutical composition having an immuno-modulating action which contains as active ingredient an immuno-modulating effective amount of one or more compounds as defined in claim 6 in a pharmaceutically acceptable carrier.

* * * * *